United States Patent
Rademacher et al.

(10) Patent No.: US 7,771,342 B2
(45) Date of Patent: Aug. 10, 2010

(54) APPARATUS AND METHOD FOR REDUCING VISION PROBLEMS AS A RESULT OF FLOATERS

(75) Inventors: Patrick J. Rademacher, 15411 Germanium St. NW., Ramsey, MN (US) 55303-4745; JoAnn K. Rademacher, Ramsey, MN (US); Jason D. Smith, Minneapolis, MN (US); Charles A. Lemaire, Apple Valley, MN (US)

(73) Assignee: Patrick J. Rademacher, Ramsey, MN (US)

( * ) Notice: Subject to any disclaimer, the term of this patent is extended or adjusted under 35 U.S.C. 154(b) by 935 days.

(21) Appl. No.: 11/238,545

(22) Filed: Sep. 28, 2005

(65) Prior Publication Data

US 2006/0069420 A1    Mar. 30, 2006

Related U.S. Application Data

(60) Provisional application No. 60/614,882, filed on Sep. 29, 2004.

(51) Int. Cl.
*A61N 1/00* (2006.01)
(52) U.S. Cl. ...................................... 600/15
(58) Field of Classification Search ............... 600/9–15
See application file for complete search history.

(56) References Cited

U.S. PATENT DOCUMENTS

| 4,197,840 A | * | 4/1980 | Beck et al. ............. 606/204.25 |
| 4,391,270 A | | 7/1983 | Uragami |
| 4,798,194 A | | 1/1989 | Amishima |
| 4,841,954 A | * | 6/1989 | Kalsi ............................ 601/71 |
| 5,158,526 A | * | 10/1992 | Bricot ............................ 600/9 |
| 5,389,981 A | * | 2/1995 | Riach, Jr. ..................... 351/158 |
| 5,662,925 A | | 9/1997 | Ebert et al. |
| 5,792,176 A | | 8/1998 | Chang |
| 5,800,402 A | | 9/1998 | Bierman |
| 5,823,938 A | * | 10/1998 | Hernandez ................... 600/15 |

(Continued)

OTHER PUBLICATIONS

ACUXO, Acupuncture Research & Resource, Feb. 17, 2003, http://www.acuxo.com/meridianPictures.asp?point=ST1&meridian=Stomach, Stomach Acupuncture.*

(Continued)

*Primary Examiner*—Samuel G Gilbert
(74) *Attorney, Agent, or Firm*—Charles A. Lemaire; Lemaire Patent Law Firm, P.L.L.C.

(57) ABSTRACT

An apparatus and method for treating floater problems of the eye. In some embodiments, a magnet is non-invasively held in place against the face, and in particular, over the lower eyelid of the patient over an extended period of time, in order to control the position of the floaters and to stimulate the eye to better focus. In other embodiments, the device is included in eyeglasses that hold the magnet next to the lower eyelid. In some embodiments, the magnet is placed next to the lower eyelid. In some embodiments, the magnet is replaced by or supplemented with electrical stimulation. Some embodiments use a permanent magnet, while others use an AC or DC electromagnet. In some embodiments, a tapping device or heating device is included. The electro-magnetic force, tapping, and/or heat are controlled with a chip, circuit, and/or switch. In some embodiments, the device is placed under the skin.

16 Claims, 6 Drawing Sheets

U.S. PATENT DOCUMENTS

| | | | |
|---|---|---|---|
| 6,344,021 B1 * | 2/2002 | Juster et al. | 600/15 |
| 6,406,419 B1 * | 6/2002 | Farahmand | 600/15 |
| 6,506,403 B1 | 1/2003 | Yu | |
| 6,579,222 B2 * | 6/2003 | Mann | 600/15 |
| D477,412 S | 7/2003 | Miles | |
| 6,611,962 B2 | 9/2003 | Redwood et al. | |
| 6,632,168 B2 | 10/2003 | Roberts et al. | |
| 2004/0010178 A1 * | 1/2004 | Buckner | 600/9 |
| 2006/0122455 A1 * | 6/2006 | Lee | 600/15 |

OTHER PUBLICATIONS

Palmer, B. J., Invisible Force Traditional Magnetic Therapy A consensus of Practical Opinion, five copied pages, 1997.*

* cited by examiner

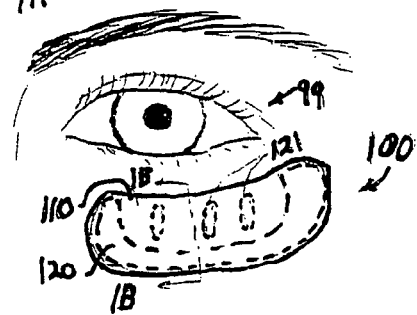
FIG. 1A
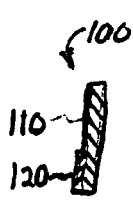
FIG. 1B
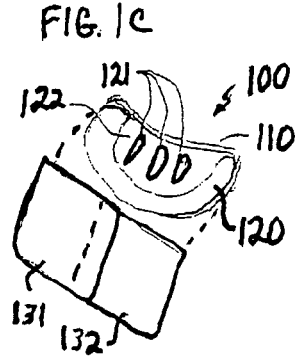
FIG. 1C
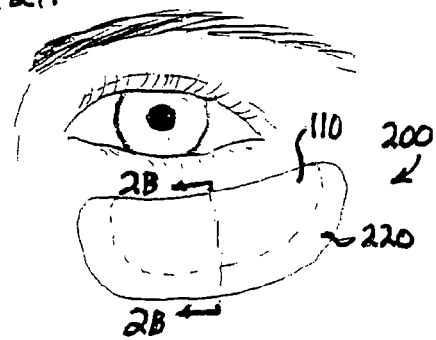
FIG. 2A
FIG. 2B
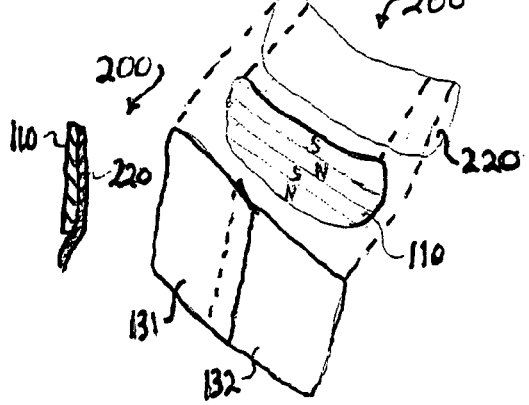
FIG. 2C
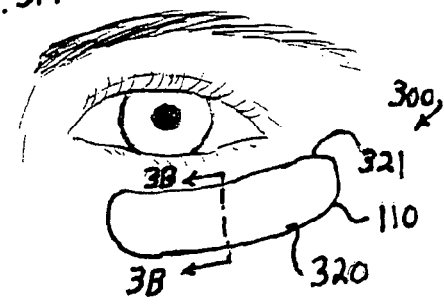
FIG. 3A
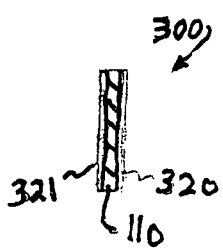
FIG. 3B
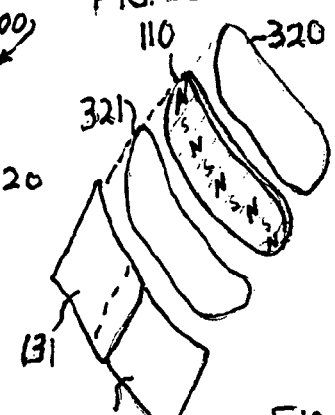
FIG. 3C
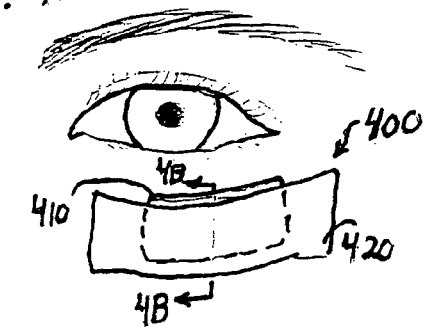
FIG. 4A
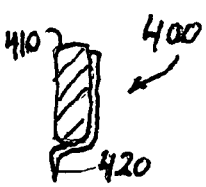
FIG. 4B
FIG. 4C

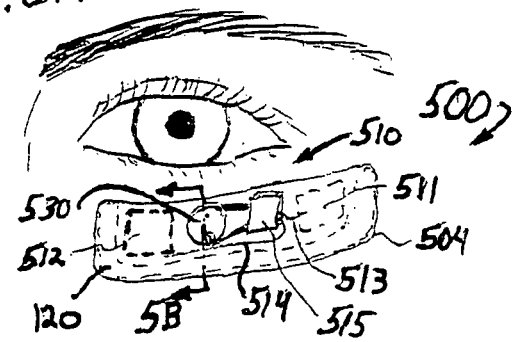
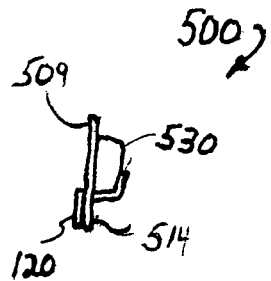
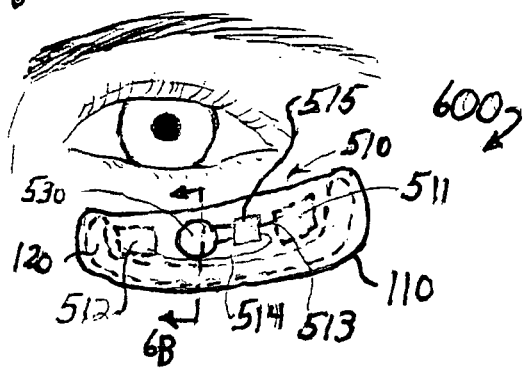
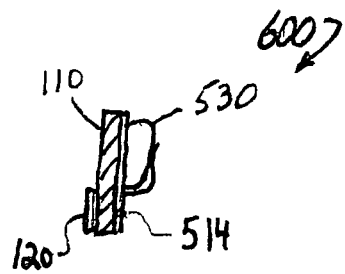
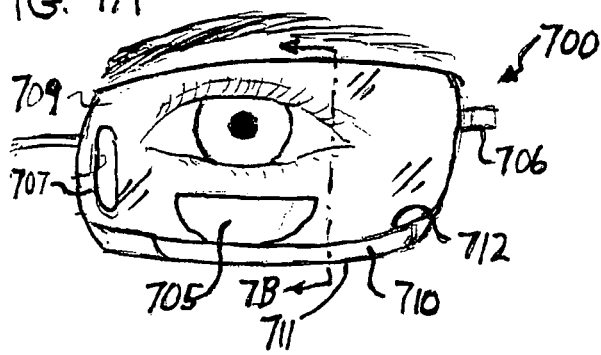
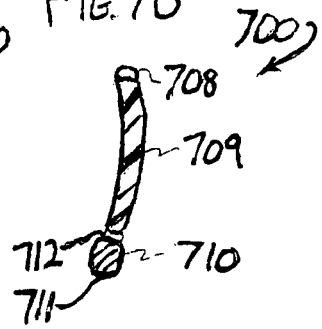
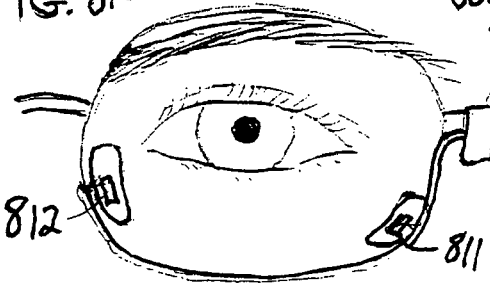
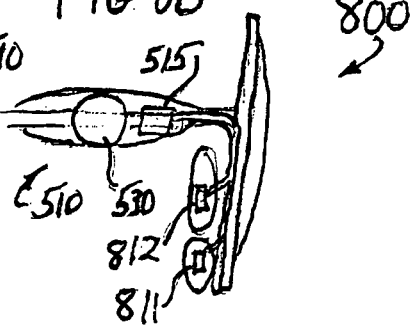

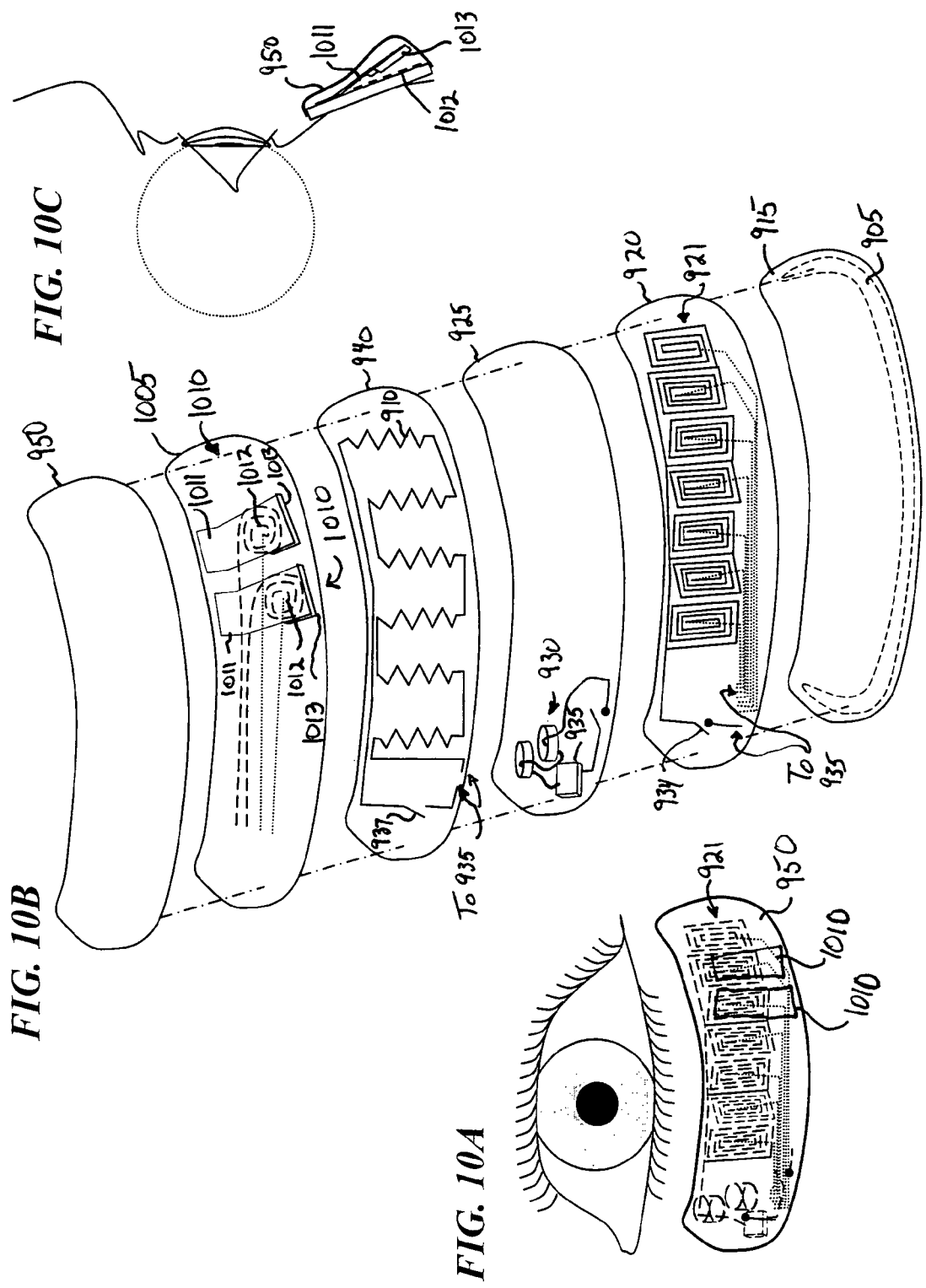

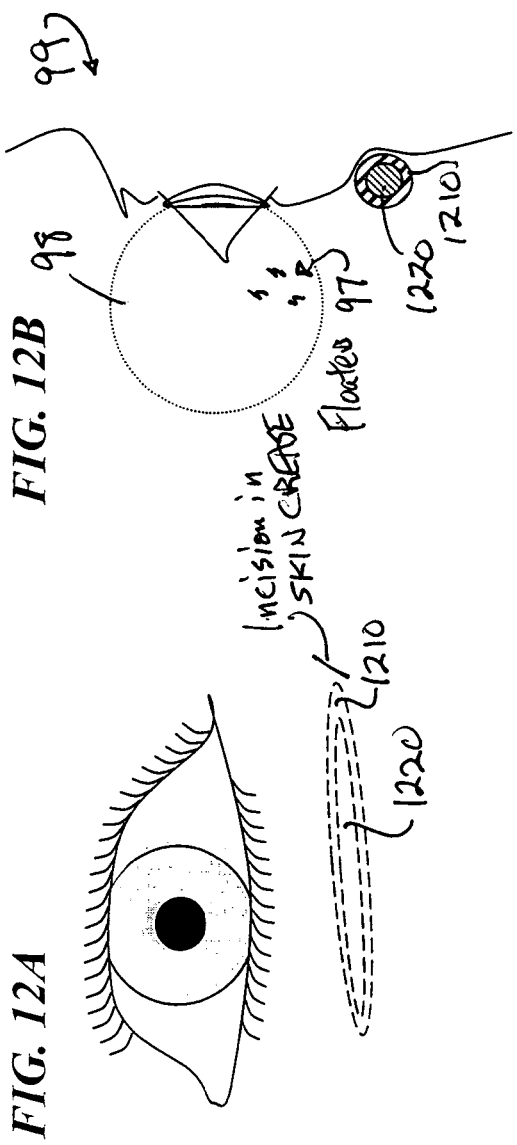
FIG. 12A
FIG. 12B
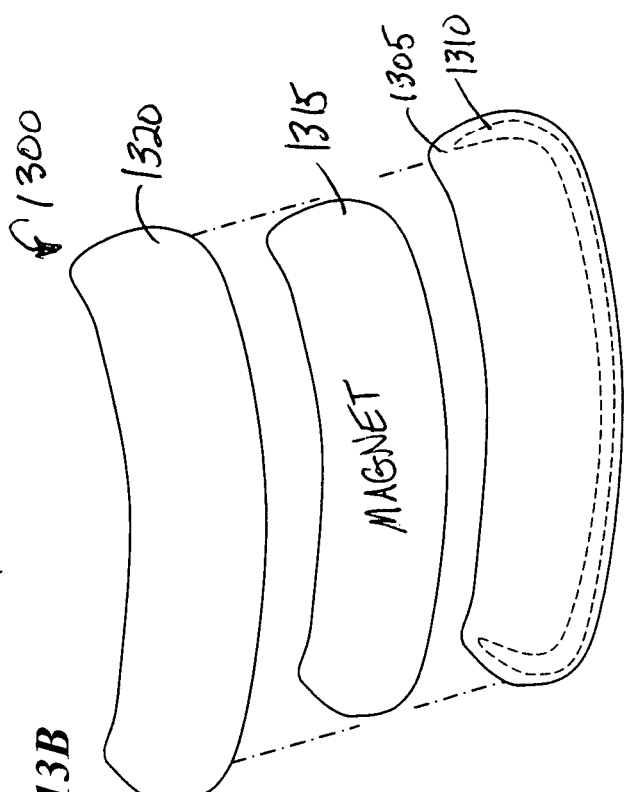
FIG. 13B
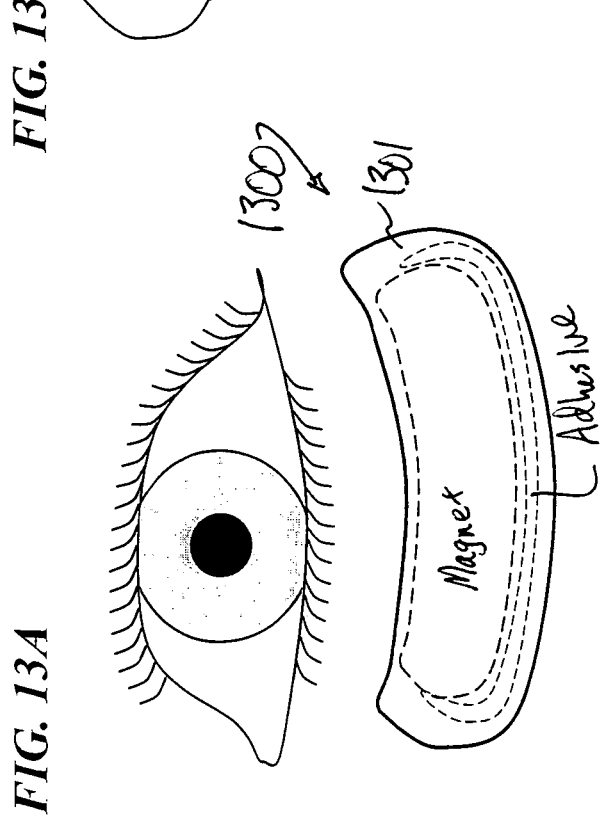
FIG. 13A

APPARATUS AND METHOD FOR REDUCING VISION PROBLEMS AS A RESULT OF FLOATERS

CROSS-REFERENCE TO RELATED INVENTION

This invention claims benefit of U.S. Provisional Patent Application 60/614,882 filed Sep. 29, 2004, which is hereby incorporated by reference in its entirety.

FIELD OF THE INVENTION

This invention relates to methods and apparatus for reducing vision problems caused by floaters (a condition of the vitreous humor in the human eye), and more specifically to a non-invasive magnetic and/or electric remedy placed near the eye.

BACKGROUND OF THE INVENTION

Occasionally people will see small spots or "floaters" in their field of vision. Floaters are sometimes described as blurred spots or strands that can be seen floating through a normal field of vision, typically more pronounced against a bare wall or a blue sky. For most people, floaters do not severely impede vision. However, for some people, particularly after laser-surgery or other trauma, the problem becomes severe and prevents the ability of the eye to focus properly.

Floaters are often the result of protein deposits floating in the vitreous humor that cast shadows on the retina of the eye. This condition, often referred to as Posterior Vitreous Detachment (PVD), is a somewhat common occurrence, and is very seldom associated with retinal tears, which is a more serious condition.

At a young age the vitreous humor of the eye is typically firm and gelatinous. As a person ages, the vitreous humor goes through syneresis, the exudation of the liquid component of a gel, in which the vitreous humor resembles water more than it does a gelatinous substance. During syneresis, parts of the gel remains intact, forming chunks, and although they are clear, they cast an optical shadow on the retina, giving them a dark appearance.

Although there have been improvements made to help reduce the above problems by various means in the industry, the problems mentioned above still exist.

SUMMARY OF THE INVENTION

In some embodiments, the invention includes an apparatus and method for treating problems associated with floaters in the eye. In some embodiments, a magnet is non-invasively held in place against the face, and in particular over the lower eyelid of the patient over an extended period of time, in order to control the position of the floaters and to stimulate the eye to focus properly. In some embodiments, the device is taped to the user's face. In other embodiments, the device is included in eyeglasses that hold the magnet in place next to the lower eyelid. In other embodiments, the magnet is replaced or supplemented with electrical stimulation to the lower eyelid.

In some embodiments, the apparatus includes an electromagnet and battery operative coupled to the electromagnet. In some embodiments, this apparatus includes a series of layers wherein a first layer of hypoallergenic material is attached to a second layer, where the second layer contains an electromagnet. The second layer is attached to a third layer containing a battery operative connected to the electromagnet of the second layer. The third layer is optionally connected to a fourth layer containing a tapping device. This fourth layer is optionally connected to a heating element contained in an optional fifth layer. In some embodiments the flow of electrical current is controlled by a chip, on/off switch, function-selection switch, or some combination thereof.

In some embodiments, a therapeutic kit for the treatment of an eye problem is provided. In some embodiments, the kit includes a holder for applying the apparatus to a person, and a therapy unit that supplies a therapeutically effective dose of a magnetic field or electric current or both. In some embodiments, the therapy unit is operatively coupled to the holder so that the holder maintains the unit in a therapeutically effective position for treatment of the eye problem. In some embodiments, the therapy unit of the kit includes a magnet. In still further embodiments, the kit includes a holder with a biocompatible releasable adhesive for holding at least a portion of the magnet against the skin of a lower eyelid. In some embodiments, wherein the holder includes a bio-compatible adhesive material configured to hold to the user's skin when in use, but later readily release from the user's skin when removal is desired.

In some embodiments, a skin-contact surface of the magnet is coated with a hypoallergenic material to prevent migration of material from the magnet to the user's skin. In some embodiments, the magnet in the kit is made of a magnetized synthetic rubber. In some embodiments, the therapy unit of the kit includes a transcutaneous electrical stimulation unit. In some embodiments, the therapy unit of the kit includes a transcutaneous electrical nerve stimulation unit having an output designed to stimulate nerve responses. Other embodiments of the kit include the therapy unit with a magnet (some embodiments use a permanent magnet having alternating north and south poles, other embodiments use an electromagnet assembly having a plurality of coils whose winding direction and electrical current direction forms alternating north and south poles). In some embodiments, the kit and the holder contained therein include eyeglasses.

In some embodiments, an apparatus for the treatment of an eye problem is disclosed that includes a holder for applying the apparatus to a person, a therapy unit that supplies a therapeutically effective dose of a magnetic field or electric current or both. This unit, in some embodiments, is operatively coupled to the holder so that the holder maintains the unit in a therapeutically effective position for treatment of the eye problem. In some embodiments, holder includes eyeglasses. In some embodiments, the holder includes a Transcutaneous Electrical Stimulation unit. In some embodiments, a magnet encased in a sterile plastic material is also included. In still other embodiments, a therapy unit includes a magnet, a bio-compatible releasable adhesive for holding at least a portion of the magnet against the skin of a lower eyelid, and a skin-contact surface of the magnet coated with a hypoallergenic material to prevent migration of material from the magnet to a user's skin. In some embodiments, the therapy unit includes a thermal compress. In some embodiments, the magnet is made of a rare-earth metal such as Neodymium.

In some embodiments, a therapy unit includes a battery operatively coupled to an electromagnet. In some embodiments, the therapy unit includes a heating element operatively couple to the battery. In some embodiments, electrical current from the battery is controlled by a switch. In some embodiments, the therapy unit is operatively coupled to eyeglasses.

In some embodiments, a therapy unit includes a first layer of hypoallergenic material, a second layer attached to the first layer, where the second layer contains an electromagnet, and a third layer attached to the second layer, the third layer containing a battery operatively connected to the electromagnet in the second layer. In some embodiments, a fourth optional layer is secured to the third layer, the fourth layer containing a heating element operatively connected to the battery of the third layer. Some embodiments include a fifth optional layer secured to the fourth layer, the fifth layer containing a tapping device operatively connected to the battery of the third layer. In some embodiments of the therapy unit, the first layer includes 3M™ Micropore™ or a similar micropore-type tape. In some embodiments, a material substantially similar to Breathe Right™ nasal strips (available from CNS, Inc. of Minneapolis, Minn.) is used. In some embodiments, the therapy unit is operative connected to a user's skin with an adhesive material. In some embodiments, the battery connection of the therapy unit is controlled by a switch. In some embodiments, the therapy unit is operatively coupled to eyeglasses.

In some embodiments, a method of treating an eye problem includes applying a field to an outer surface of an eyelid of a person with an eye problem, maintaining the field in position as the person uses an eye for seeing, and maintaining of the field in a position including adhering a lower edge and at least one side edge but not a top edge of a therapy unit to the lower eyelid of the person. In some embodiments, the field includes magnetic and/or electrical components. In some embodiments, the therapy unit is operatively coupled to eyeglasses.

In some embodiments, an apparatus for treating an eye problem includes a means for generating a field; and an adhering means to maintain the field in a therapeutically effective position for treatment of the eye problem. In still other embodiments, the apparatus includes a means for attaching the apparatus to a pair of eyeglasses.

BRIEF DESCRIPTION OF THE DRAWINGS

FIG. 1A is a plan view that illustrates a magnetic-therapy device 100 according to some embodiments of the invention.

FIG. 1B is a cross-sectional view of magnetic-therapy device 100.

FIG. 1C is an exploded perspective view of magnetic-therapy device 100.

FIG. 2A is a plan view that illustrates a magnetic-therapy device 200 according to some embodiments of the invention.

FIG. 2B is a cross-sectional view of magnetic-therapy device 200.

FIG. 2C is an exploded perspective view of magnetic-therapy device 200.

FIG. 3A is a plan view that illustrates a magnetic-therapy device 300 according to some embodiments of the invention.

FIG. 3B is a cross-sectional view of magnetic-therapy device 300.

FIG. 3C is an exploded perspective view of magnetic-therapy device 300.

FIG. 4A is a plan view that illustrates a magnetic-therapy device 400 according to some embodiments of the invention.

FIG. 4B is a cross-sectional view of magnetic-therapy device 400.

FIG. 4C is an exploded perspective view of magnetic-therapy device 400.

FIG. 5A is a plan view that illustrates an electronic-therapy device 500 according to some embodiments of the invention.

FIG. 5B is a cross-sectional view of electronic-therapy device 500.

FIG. 6A is a plan view that illustrates a magnetic-electronic-therapy device 600 according to some embodiments of the invention.

FIG. 6B is a cross-sectional view of magnetic-electronic-therapy device 600.

FIG. 7A is a plan view that illustrates a magnetic-therapy device 700 according to some embodiments of the invention.

FIG. 7B is a cross-sectional view of magnetic-therapy device 700.

FIG. 8A is a plan view that illustrates an electronic-therapy device 800 according to some embodiments of the invention.

FIG. 8B is a cross-sectional view of electronic-therapy device 800.

FIG. 10A is a plan view of an electro-magnetic therapy device 1000.

FIG. 10B is an exploded perspective view of an electromagnetic therapy device 1000, with an electronically powered tapping device 1010.

FIG. 10C is a cross-sectional view of electronic-therapy device 1000.

FIG. 12A is a plan view of an implantable magnetic therapy device 1200, according to some embodiments of the invention.

FIG. 12B is a cross sectional view of an implantable magnetic therapy device 1200.

FIG. 13A is a plan view of a magnetic therapy device 1300 of some embodiments of the invention.

FIG. 13B is an exploded perspective view of a magnetic therapy device 1300.

DETAILED DESCRIPTION OF THE INVENTION

Figure 9B:
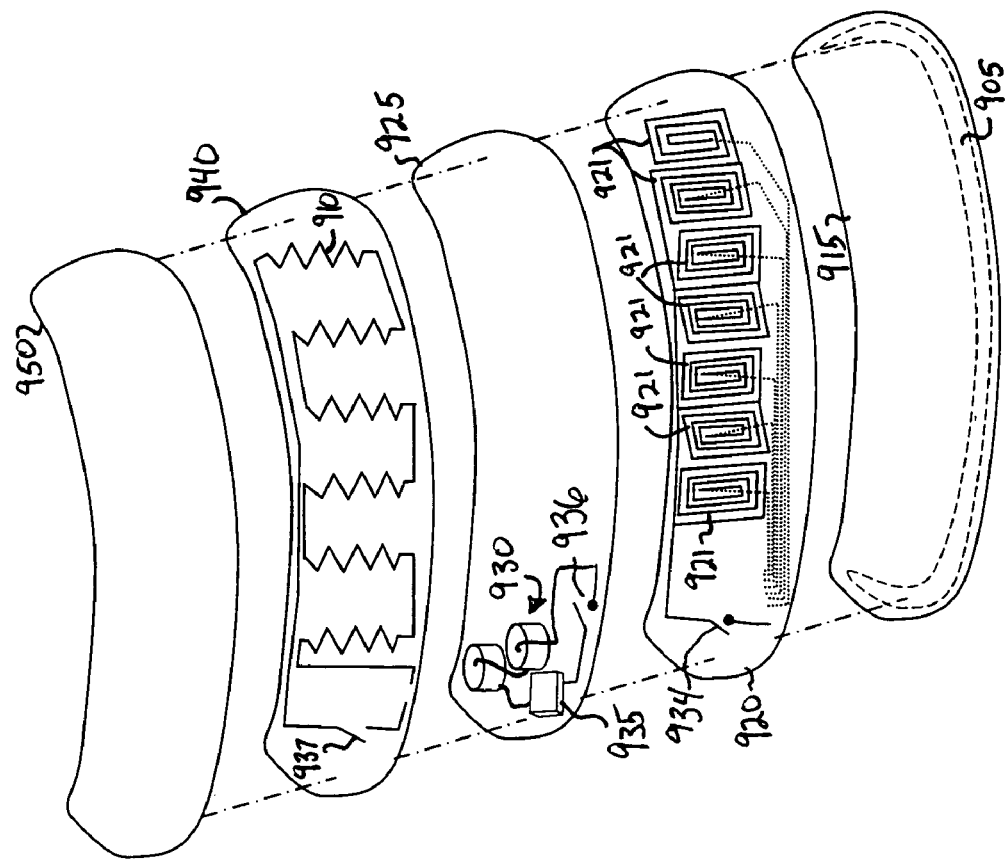
FIG. 9B is an exploded perspective view of an electromagnetic therapy device 900.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

In some embodiments, the invention utilizes the rubberized magnetic material typically used to make "refrigerator magnets," which typically includes a series of alternating north and south poles.

In some embodiments, the number of magnetic fields influencing the eye varies relative to the orientation of the magnet to the eye. For example, if a magnet is placed parallel to the eye lid the number of magnet fields influencing the eye will be spread out over a larger area of the eye. If, however, the end of the magnet is placed perpendicular to the eye lid, the intensity of the magnetic waves influencing the eye will be much greater, but over a much more limited area of the eye. In some embodiments, the magnet of the present invention is oriented parallel to the eye lid, whereas in other embodiments the magnet will be oriented perpendicular to the eye lid.

With regard to the relative strength of a magnet, the force or attractive strength ("S") of a magnet drops off relative to the inverse cube of the distance ("D") from the magnet. This relationship can be represented as:

$$S=1/D^3$$

For example, if the distance from a magnet is doubled, the strength of a magnet will decrease by a factor of eight. Thus, in some embodiments, not only is the orientation of the magnet important, but it is also important to place the magnet as close as possible to the eye that one is seeking to influence with the magnet.

For the purpose of this invention, the term field can refer to an electrical field or a magnetic field.

FIG. 1A is a plan view that illustrates a magnetic device 100 according to some embodiments of the invention. In some embodiments, device 100 includes a magnet 110 that generates a magnetic field, and a layer of adhesive 120.

In some embodiments, adhesive 120 is a hypoallergenic adhesive. In some embodiments, adhesive 120 is placed primarily or exclusively on the lower edge and the side edges of magnet 110, and little or no adhesive is placed along the center and top edge of magnet 110. This allows easier removal of device 100, since adhesive near the very pliable edge of the eyelid painfully pulls out on the eyelid, rather than releasing, when removal of the device is attempted.

In some embodiments, magnet 110 is coated with a very thin layer of hypoallergenic material such as a polymer (for example, some magnets contain nickel to which some persons are allergic), at least on the surface that will be in contact with the person's skin. In some embodiments, magnet 110 is cut from a pliable magnetized (rubber-like) material (as are conventionally used as "refrigerator magnets" for decoration or advertisements). In some embodiments, these refrigerator magnets typically have a magnetic strength of approximately 200 gauss ("G"). In some embodiments, the edge shape of magnet 110 is cut to provide a shape compatible with being placed in close proximity to the edge of the eyelid. In some such embodiments, magnet 110 is cut or formed with a concave upper edge that can be placed to conform in close proximity to the edge of the lower eyelid of the person. This allows higher magnetic field strength in the eye, and also allows the largest field of sight. This concave upper edge allows the magnet to be placed closer to the eye 99 than other shapes, in order to non-invasively increase magnetic field strength in the eye. In some such embodiments, the corners, sides, and lower edge are convex rounded shapes for comfort. In some embodiments, device 100 is designed to be placed 1, 2, or 3 mm from the edge of the eyelid. This is far enough such that the device does not rise up and block vision when the person smiles or otherwise causes the lower eyelid to rise.

It has been found by the inventors that, immediately following laser surgery to reattach a detached retina, there is sometimes a huge increase in the number and size of "floaters" and cloudiness in the field of vision, sometimes to such a large extent that it becomes impossible for the eye to focus. After applying device 100, 200, 300, 400, 500, or 600 of the present invention, the floaters are "controlled" at least to an extent that allows the eye to again focus properly. Further, when a very strong magnet is used in a configuration such as shown in FIG. 4, the floaters appear to move faster than when a weaker magnet is used. Usually, it takes 20 to 30 minutes after applying the magnetic device of FIGS. 1A-4A for the effect to become noticeable. Further, if the device is removed, the problem returns and it is again difficult to focus. In some embodiments, extremely thin lines of additional adhesive 121 are provided to slightly stick the upper and central portions of magnet 110 to the skin, while other embodiments omit these to make the device 100 easier to remove.

In some embodiments, device 100 is applied upon waking and worn all the time the patient is awake, in order to improve vision and reduce the problems in seeing that are due to floaters. Device 100 is then removed just before sleep.

In some embodiments, magnet 110 is replaced by a stiff but pliable piece of cardstock or plastic. In some embodiments, the embodiment using magnet 110 works much better at treating the problem of inability to focus than the embodiment having the cardstock or plastic replacement.

FIG. 1B is a cross-sectional view of magnetic-therapy device 100 along section line 1B of FIG. 1A. In some embodiments, the outside surface of device 100 (the side facing outward when the device 100 is applied to the face) is colored to a skin tone color and a dull or waxy texture, in order to be less noticeable.

FIG. 1C is an exploded perspective view of magnetic-therapy device 100. In some embodiments, release-layer strips 131 and 132 are applied during manufacture, and device 100 is wrapped in suitable removable paper and sterilized in the manner used for Band-Aid™ type finger bandages. The paper package is opened by the consumer, strips 131 and 132 are removed, and device 100 is applied to the face just under the affected eye.

In some embodiments, a sterile gauze pad is attached in the area 122, and a medicament is optionally applied. This is useful for situations where other trauma or disease (such as plastic surgery to the eyelid or "pinkeye") needs to be treated.

FIG. 2A is a plan view that illustrates a magnetic-therapy device 200 according to some embodiments of the invention. Device 200 is used in the same manner as device 100. Device 200 provides a magnet 110, which can be the same size as used in FIG. 1A, but which has its entire back surface against the skin of the patient, and has a piece of (e.g., fabric) adhesive substrate 220 covering its front (outer) surface, with adhesive substrate 220 extending below and to the sides of magnet 110. In some embodiments, adhesive substrate 220 is a skin-toned dull surface fabric such as used for fabric finger bandages.

FIG. 2B is a cross-sectional view of magnetic-therapy device 200 along section line 2B of FIG. 2A.

FIG. 2C is an exploded perspective view of magnetic-therapy device 200. In some embodiments, magnet 110 has north-south alternating striped of magnetic material as shown.

FIG. 3A is a plan view that illustrates a magnetic-therapy device 300 according to some embodiments of the invention. In some embodiments, device 300 has a magnet 110 with a weak adhesive layer 321 covering its entire skin-side surface. In some embodiments, outer layer 320 includes a skin-toned dull surface fabric such as used for fabric finger bandages.

FIG. 3B is a cross-sectional view of magnetic-therapy device 300 along section line 3B of FIG. 3A.

FIG. 3C is an exploded perspective view of magnetic-therapy device 300. In some embodiments, magnet 110 has north-south alternating striped of magnetic material as shown.

FIG. 4A is a plan view that illustrates a magnetic-therapy device 400 according to some embodiments of the invention. In some embodiments, magnet 410 is an extremely strong (upwards of 10,000 G) rare-earth magnet such as used in the voice coil actuators of modern computer hard-disk drives. In some embodiments, a piece of hypoallergenic medical tape 420 hold magnet 410 in place, to create a therapeutically effective dose of a magnetic field, and tape 420 maintains the device 400 in a therapeutically effective position for treatment of the eye problem. In some embodiments, magnet 410 has its north or south pole facing the skin, and the opposite pole facing outward.

FIG. 4B is a cross-sectional view of magnetic-therapy device 400 along section line 4B of FIG. 4A.

FIG. 4C is an exploded perspective view of magnetic-therapy device 400.

FIG. 5A is a plan view that illustrates an electronic-therapy device 500 according to some embodiments of the invention. In some embodiments, device 500 includes a strip of hypoallergenic material 509, an electric-therapy unit 510 having a battery 530, circuit 515 (in some embodiments, an electronic chip that converts the power from battery 530 into electrical pulses that are applied to the skin), electrical skin pads 511 and 512, and pad wires 513 and 514. In some embodiments, circuit 515 increases the voltage of the pulses to a therapeutically effective value and provides the pulses at a therapeutically effective frequency. In some embodiments, adhesive 120 is a hypoallergenic adhesive. In some embodiments, adhesive 120 is placed primarily or exclusively on the lower edge and the side edges of device 500, and little or no adhesive is placed along the center and top edge of device 500. This allows easier removal of device 500, since adhesive near the very pliable edge of the eyelid painfully pulls out on the eyelid, rather than releasing, when removal of the device is attempted.

In some embodiments, therapy unit 510 includes a Transcutaneous Electrical Stimulation unit. In some embodiments, therapy unit 510 includes a Transcutaneous Electrical Nerve Stimulation unit.

FIG. 5B is a cross-sectional view of electronic-therapy device 500 along section line 5B of FIG. 5A.

FIG. 6A is a plan view that illustrates a magnetic-electronic-therapy device 600 according to some embodiments of the invention. In some embodiments, device 600 is a combination of device 100 of FIG. 1A providing a magnetic field, and an electronic-therapy device 500 of FIG. 5A providing a series of electric pulses to the skin. In other embodiments, other combinations of the electronic-therapy devices described herein are combined synergistically with the magnetic-therapy devices described herein are used.

FIG. 6B is a cross-sectional view of magnetic-electronic-therapy device 600 along section line 6B of FIG. 6A.

FIG. 7A is a plan view that illustrates a magnetic-therapy device 700 according to some embodiments of the invention. In some embodiments, device 700 includes a magnet 710 held in eyeglasses of the user in a position such that magnet 710 is held against or very near to the skin of the user. In some embodiments, magnet 710 is primarily at the lower rim of the eyeglasses and held against the lower eyelid of the user by rim holders 712 and 711. In other embodiments, the upper rim or the entire rim includes a magnet 710. Lens 709 is held between upper rim 708 and lower rim 712. In some embodiments, a bifocal 705 or other lens enhancement is provided. In some embodiments, the center of lens 709 is clear and the periphery of lens 709 is tinted, translucent, or opaque, in order that vision is concentrated in the center of the field of view for therapeutic or cosmetic reasons. In some embodiments, lens 712 is tinted (as in sunglasses) to provide additional relief for the user, which is particularly useful after surgery, such as retina reattachment surgery. In some embodiments, nosepiece 707 and/or earpiece 706 are also magnetic, to provide additional magnetic field at specific locations that are therapeutically effective.

FIG. 7B is a cross-sectional view of magnetic-therapy device 700 along section line 7B of FIG. 7A.

FIG. 8A is a plan view that illustrates an electronic-therapy device 800 according to some embodiments of the invention. In some embodiments, device 800 is integrated with the user's eyeglasses, and has electric skin nose-pad 812 and cheek-pad 811 used to non-invasively apply electric pulses from electric-therapy unit 510 across the skin of the user around or below the eye. In some embodiments, device 800 is a magnetic-electronic-therapy device, and includes a magnet in nose-pad 812 and/or cheek-pad 811. In some embodiments, a magnet 710 such as shown and described in FIG. 7A is also or alternatively used.

FIG. 8B is a cross-sectional view of electronic-therapy device 800.

Some embodiments of the invention include a method and apparatus for the treatment of an eye problem that includes a holder for applying the apparatus to a person; and a therapy unit that supplies a therapeutically effective dose of a magnetic field or electric current or both, the unit operatively coupled to the holder so that the holder maintains the unit in a therapeutically effective position for treatment of the eye problem. In some embodiments, the therapy unit includes a magnet. In some embodiments, the holder includes a biocompatible releasable adhesive for holding at least a portion of the magnet against the skin of a lower eyelid. In some embodiments, a skin-contact surface of the magnet is coated with a hypoallergenic material to prevent migration of material from the magnet to the user's skin. In some embodiments, the magnet is made of a magnetized synthetic rubber. In some embodiments, the therapy unit includes a Transcutaneous Electrical Nerve Stimulation unit. In some embodiments, the therapy unit further includes a magnet. In some embodiments, the holder of the magnetic unit includes eyeglasses. In some embodiments, the holder of the electronic unit includes eyeglasses.

In some embodiments, the apparatus for the treatment of an eye problem includes an electromagnet, with a magnetic force in the 200 G to 10,000 G range, coated with a very thin layer of hypoallergenic material such as a polymer (for example, some magnets contain nickel to which some persons are allergic), where that electromagnet would otherwise be in contact with the person's skin. In some embodiments, this electromagnet typically will be placed in contact with the person's skin no closer than about one-quarter inch (about 0.64 cm) from the lower eyelid. In some embodiments, this apparatus possess a bio-compatible releasable adhesive applied to the edges of the apparatus to allow for the apparatus to be positioned below the user's lower eye lid. Additionally, in some embodiments, the electromagnet will be oriented such that it is parallel to the lower eye lid, while in other embodiments it will be perpendicular to the lower eye lid. This electromagnet is operatively coupled via a circuit to a battery and accompanying off/on switch that provides electrical power to the electromagnet. The electromagnet, in turn, provides magnetic pulses to the eye through the skin. In still other embodiments, an electronic chip is used to convert the power from the battery into magnetic pulses that are applied to the skin. In some embodiments, this battery is of the Lithium-ion variety. In still other embodiments, an adjustable circuit controlling the amount of electricity flowing (i.e., such that the flow can be increased or decreased under control of the user) from the battery to the electromagnet is interposed between the electromagnet and the battery. In some embodiments, this switch acts to control the frequency and magnitude of magnetic pulse provided at the point of contact with the user's skin and ultimately the user's eye. In some embodiments, the coupling of the electromagnet, battery, and switch or chip is enclosed in a hypoallergenic material, with the on/off or adjustable switch mounted internally or externally to this hypoallergenic material.

Figure 9A:
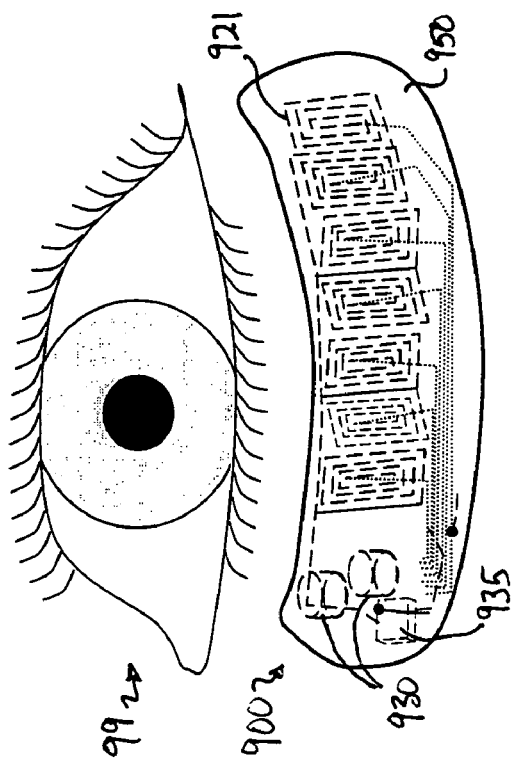
FIG. 9A is a plan view of an electromagnetic therapy device 900.

FIG. 9A is a plan view of an electromagnet therapy device 900 used in some embodiments of the invention. Depicted is an outer or top layer 950 of a hypoallergenic material 950 visible when the device is applied to the skin of user 99.

FIG. 9B is an exploded perspective view of an electromagnetic-therapy device 900 according to some embodiments of the invention. In some embodiments, the apparatus includes an adhesive layer 905, and electromagnet 921 and/or an electrically powered heat-generating element 910. In some embodiments, heating element 910 is secured and operatively connected to the apparatus in a series of layers, wherein a first layer 915 of hypoallergenic material would be in contact with the skin. A second layer 920 containing an electromagnet 921 is operatively secured to the first layer 915. In some embodiments, electromagnet 921 includes one or more narrow helical coils that, if more than one coil, alternate in a clockwise/counterclockwise orientation in order to generate alternating north and south poles pointing in the direction of patient 99. In some embodiments, a switch 934 is operable to connect or disconnect the coils, while in other embodiments, circuit 935 performs this function. A third layer 925 that includes battery 930 is operatively connected to the second layer 920 so as to provide electrical power to the electromagnet via a circuit 935. In some embodiments, an on-off switch 936 and/or a controller circuit 935 are also included in third layer 925. In some embodiments, the circuit 935 provides alternating (plus and minus) pulses to the electromagnets. In other embodiments, a DC magnetic field is generated. In some embodiments, a fourth layer 940 having heating element 910 is operatively connected to the third layer 925 and receives electrical power from the battery 930 as controlled via a circuit 935. In some embodiments, battery 930 is operatively connected and disconnected to heater 910 using off/on switch 937. In still other embodiments, the amount of heat generated by heating element 910 is adjustable using circuit 935 and is operatively coupled to the battery 930 for the apparatus via circuit 935. In some embodiments, the fourth layer is covered and sealed using hypoallergenic cover material 950. In other embodiments, the order of the layers is different than that shown (e.g., the heating element 910 and/or electromagnet coils 921 are deposited directly on base layer 915). In other embodiments, two or more of the functions above are combined onto a single layer, reducing the number of separate layers needed.

FIG. 10A is a plan view of an electromagnetic therapy device 1000, which is similar in some ways to device 900 of FIG. 9A, but with an optional electronically powered tapping device 1010.

FIG. 10B is an exploded perspective view of an electromagnet-therapy device 1000. In some embodiments, the apparatus 1000 is substantially similar to device 900 of FIG. 9B, but also includes an additional fifth layer (substrate) 1005 with one or more enclosed electrically powered tapping devices 1010 that provide a uniform tapping sensation at the point of contact with the user's skin. In some embodiments, a spring-type stiff plastic sheet 1011 is attached at one end to substrate 1005, and bent at an angle from substrate 1005, and has a piece of permanent magnet (or non-magnetized magnetic material) 1013 affixed to the distal cantilevered end of spring-type stiff plastic sheet 1011. In some embodiments, an electromagnet coil 1013 is periodically energized to attract magnetic material 1013, which then "taps" with a force that is transmitted to the skin of user 99. It is believed that the tapping and/or heat help to move the floaters in the eye towards the magnetic field and thus out of the user's vision field.

In some embodiments, this tapping has a frequency of one to five or more taps per second, with every tap having a force of less than or equal to about 2.85 gf (gram-force) or about 28 milliNewtons. In other embodiments, the frequency ranges from about one tap per 60 seconds or more, to one tap per second (e.g., in some embodiments, about 1 tap per 60 seconds, about 1 tap per 50 seconds, about 1 tap per 40 seconds, about 1 tap per 30 seconds, about 1 tap per 20 seconds, about 1 tap per 10 seconds, about 1 tap per 9 seconds, about 1 tap per 8 seconds, about 1 tap per 7 seconds, about 1 tap per 6 seconds, about 1 tap per 5 seconds, about 1 tap per 4 seconds, about 1 tap per 3 seconds, about 1 tap per 2 seconds, about 1 tap per 1 second, about 1 tap per 0.9 seconds, about 1 tap per 0.8 seconds, about 1 tap per 0.7 seconds, about 1 tap per 0.6 seconds, about 1 tap per 0.5 seconds, about 1 tap per 0.4 seconds, about 1 tap per 0.3 seconds, about 1 tap per 0.2 seconds, about 1 tap per 0.1 seconds, or within a range between any two of the above rates). In some embodiments, two or more tapping units are alternately activated at a rate as described above. In some embodiments, the frequency and force of the tapping, and its efficacy, is empirically determined, while in still other embodiments various forms of computer-aided modeling will be used to determine this force. In still other embodiments, the frequency and force of this tapping is adjustable as controlled by chip 935 that is operatively coupled to a battery 930 for the apparatus.

FIG. 10C is a cross-sectional view of electronic-therapy device 1000. Magnetic material 1013 is affixed to a cantilevered end of spring plastic sheet 1011, and periodically tapped by energizing coil 1012 under the control of chip 935.

Figure 11C:
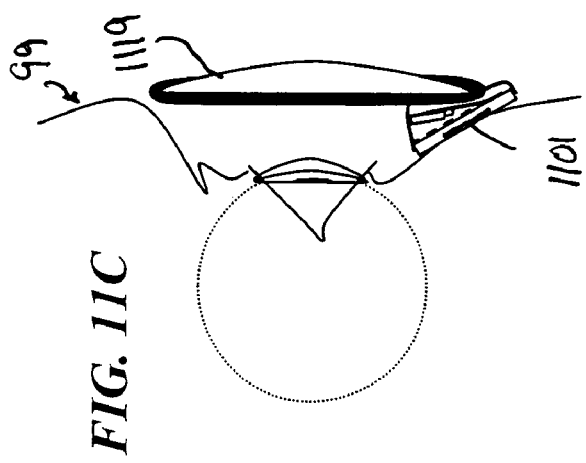
FIG. 11C is a side cross-sectional view of an electronic therapy device 1100.
Figure 11B:
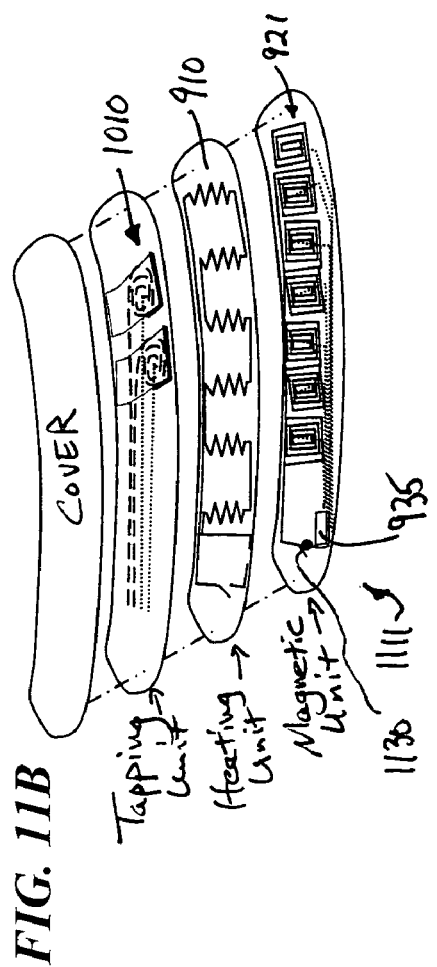
FIG. 11B is a side view of an electronic-therapy device 1100.
Figure 11A:
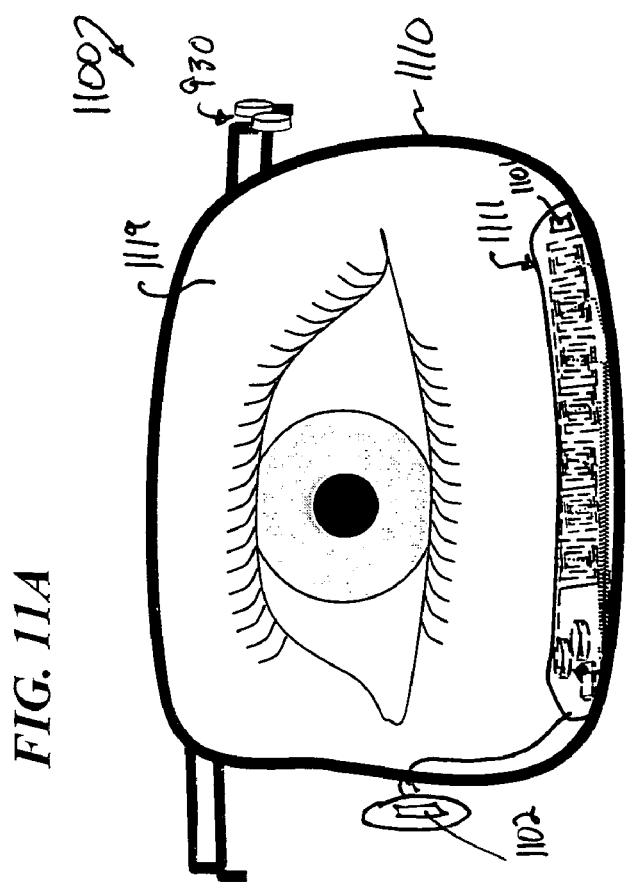
FIG. 11A is a plan view illustrating an electronic-therapy device 1100.

FIG. 11A is a plan view that illustrates an electronic-therapy device system 1100 according to some embodiments of the invention. In some embodiments, the electronic therapy device 1111 is integrated with the user's eyeglasses 1110. In some embodiments, device 1100 is integrated with the user's eyeglasses 1110, and has one or more electromagnetic skin cheek pad 1101 and/or nose pad 1102 used to non-invasively apply electric pulses from circuit 935 across the skin of the user around or below the eye.

FIG. 11B is an exploded perspective view of an electronic therapy device 1100. In some embodiments, the apparatus 1111 is substantially similar to device 1000 of FIG. 10B for the treatment of an eye problem, and similarly numbered features are as described above. In some embodiments, the electromagnet 921, with a magnetic force in the 200 G to 10,000 G range, is held against or very near to the skin of the user. In some embodiments, the electromagnet 921 is located primarily at the lower rim of the eyeglasses 1110 and held against the lower eyelid of the user by rim holders. In some embodiments, this electromagnet 921 typically is placed in contact with the person's skin no closer than about one-quarter inch (about 0.64 cm) from the lower eyelid. Additionally, in some embodiments, the electromagnet 921 will be oriented such that it is parallel to the lower eye lid, while in other embodiments it will be perpendicular to the lower eye lid. In still other embodiments, the upper rim or the entire rim includes an electromagnet 921. The lens is held between upper rim and lower rim. In some embodiments, a bifocal or other lens enhancement is provided. In some embodiments, the center of lens is clear and the periphery of lens is tinted, translucent, or opaque, in order that vision is concentrated in the center of the field of view for therapeutic or cosmetic reasons. In some embodiments, the lens is tinted (as in sunglasses) to provide additional relief for the user, which is particularly useful after surgery, such as retina reattachment surgery. In some embodiments, nosepiece and/or earpiece are also electromagnetic, to provide additional magnetic field at specific locations that are therapeutically effective. In some embodiments, the electromagnet 921 is operatively coupled to an adjustable switch 1130 that controls the flow (i.e., the flow can be increased or decreased by user activation of this switch) of electricity to the electromagnet 921 via a circuit 935 connected to a battery 930. The electromagnet 921, in turn, provides therapeutic magnetic pulses to the eye. In still other embodiments, an electronic chip 935 is used to convert the power from the battery into therapeutic magnetic pulses that are applied to the skin using coils 921.

In some embodiments, the apparatus and eyeglasses will include an electrically powered heating element 910 operatively coupled to the lower rim of the eyeglasses. Eyeglasses having a heating element 910 affixed to the lower rim of these eyeglasses are a component of some embodiments of the present invention and can be made using a modification of known techniques, such as those described in U.S. Pat. No. 3,140,390 ("the Smith et al. Patent"), incorporated here by reference in its entirety. The Smith et al. Patent describes a device in the form of eyeglasses with heating elements, wherein heat is applied to the user's skin by electrical heating elements ("heating pads") affixed to the rim of a pair of eyeglasses. The heating pads are operative coupled to an electrical power source such as a battery.

In some embodiments, the apparatus and eyeglasses include an electrically powered tapping device 1010 operatively coupled to a lower rim of the eyeglasses 1110 adjacent the affected eye. Some embodiments use solenoid weight 1013 that is magnetically attracted to one or more of the electromagnet coils 921 (or by dedicated coils 1012 as shown in FIG. 10B) as controlled by pulses from an electronic circuit 935 having a periodic pulsed output to provide periodic tapping forces (e.g., about one to three taps per second, or as few as one tap per two to one tap per ten seconds, in some embodiments). In other embodiments, piezo-electric of magnetorestrictive materials are used to generate the tapping forces In other embodiments, eyeglasses having a vibrating tapping device affixed to the rim of these eyeglasses can be made using various techniques, such as those described in U.S. Pat. No. 4,841,954 to Nirmal Kalsi ("the Kalsi Patent"), incorporated herein by reference in its entirety. The Kalsi Patent describes an oculofacial massager that uses an electrically powered motor with an off-center weight on its shaft as a vibration-generation mechanism connected to an eyeglass frame above the nosepiece for the purpose of messaging the eyes through the use of vibration.

In some embodiments, the magnetic force from the electromagnet 921, the heat from the heating element 910, and frequency and force of the tapping from the tapping device 1010 are derived from the electrical current of a battery 930 operatively coupled to the above units through circuit 935. In some embodiments, this flow of electrical current from the battery 930 is adjusted through the use of an adjustable switch 1130, on/off switch or a chip 935, or some combination thereof. By increasing or decreasing the flow of electricity, the user typically will receive more or less therapeutic magnetic pulses, heat and/or tapping.

FIG. 11C is a side cross-sectional view of an electronic therapy device 1100.

FIG. 12A is a plan view of an implanted magnetic therapy device 1200 of some embodiments of the invention. In some embodiments, a small lump is visible where device 1200 is implanted. In other embodiments, a flat magnet and enclosure is used, and no lump is visible. The implanted version of the magnet is preferred by some patients since only a small incision is needed, and this avoids the necessity of applying and constantly wearing an externally applied floater control device, such as described in the other figures herein.

FIG. 12B is a side cross-sectional view of magnetic therapy device 1200. In some embodiments, a permanent magnet 1220 is encased in an inert or bio-compatible plastic casing 1210, and is implanted just under the skin below the eye 98 of patient 99, in order to control floaters 97. This provides a permanent floater-control solution that is easily reversible (i.e., the device removed) by minor surgery. In some embodiments, the implantable unit 1200 includes a permanent magnet 1220 sealed in a sterile material bio-compatible 1210 (to provide a bio-compatible sterile magnet) and is implanted under the skin in the fat just below the eye socket. In some embodiments, this sterile material is a plastic or synthetic material. In some embodiments, the sterile magnet is approximately 0.5 inches long (1.27 cm), 0.06 inches (0.15 cm) thick and cylindrical in shape. In still other embodiments, the sterile magnet is 0.5 inches long (1.27 cm), 0.06 inches (0.15 cm) thick, and 0.06 inches (0.15 cm) wide and rectangular in shape. In some embodiments, the sterile magnet is placed approximately 0.125 inches (0.32 cm) below the lower edge of the eye socket. In some embodiments, the distance the sterile magnet is placed from the lower edge of the eye socket is determined through empirical testing and/or modeling. Moreover, in some embodiments, the most efficacious shape of the sterile magnet can be determined through empirical testing and/or modeling using external magnets before the surgery is performed.

In some embodiments, the present invention provides a method of placing a magnet encased in a sterile plastic material under the skin. This method includes making an incision of an appropriate size (e.g., in a skin crease, so it is less noticeable when healed) in the skin just bordering the lower edge of the eye socket, inserting the magnet 1220 that has been encased in a sterile plastic 1210 material into the incision, and closing the incision.

FIG. 13A is a plan view of a tailored magnetic therapy device 1300 of some embodiments of the invention. In some embodiments, an external layer 1301 is visible.

FIG. 13B discloses an exploded perspective view of a tailored magnetic therapy device 1300. In some embodiments, a first layer 1305 of semi-permeable tape, such as Micropore™ tape, having a selective area of adhesive 1310 is used to make a first layer. A magnet 1315 is placed onto the first layer 1305. In some embodiments, this magnet 1315 is 1.75 inches (4.45 cm) long, 0.375 inches (0.95 cm) deep, and ranges between 0.5 (1.27 cm) and 0.375 inches (0.95 cm) wide. The width of the magnet varies in relation to the curvature of the lower eye lid, following this curvature. By following this curvature the apparatus can be placed in closer relation to the lower eye lid, thus providing more therapeutic effect to the eye. In some embodiments, this magnet 1315 is sealed with a cloth or adhesive material 1320. In the embodiments shown in FIG. 13A and FIG. 13B (as well as those shown in FIGS. 1A, 2A, 5A, 6A, 9B, and 10B), the magnetic therapy device 1300 has a first surface facing away from the skin of the user 99, and a second surface facing toward the skin of user 99, with the adhesive 1310 applied to the lower edge and at least one side of the second surface, and at least half the area of the second surface of magnetic therapy device 1300 does not have adhesive and thus at least half the area of the second surface is not adhered to the skin of user 99.

In some embodiments of any of the above devices, the electromagnet has a magnetic force in the range of: 200 G and 500 G, 500 G and 1000 G, 1000 G and 1500 G, 1500 G and 2000 G, 2000 G and 2500 G, 2500 G and 3000 G, 3500 G and 4000 G, 4500 G and 5000 G, 5500 G and 6000 G, 6500 G and 7000 G, 7500 G and 8000 G, 8500 G and 9000 G, or 9500 G and 10000 G.

In some embodiments of any of the above devices, the permanent magnet has a magnetic force in the range of: 200 G and 500 G, 500 G and 1000 G, 1000 G and 1500 G, 1500 G and 2000 G, 2000 G and 2500 G, 2500 G and 3000 G, 3500 G and 4000 G, 4500 G and 5000 G, 5500 G and 6000 G, 6500 G and 7000 G, 7500 G and 8000 G, 8500 G and 9000 G, or 9500 G and 10000 G.

In some embodiments, a therapeutic kit for the treatment of an eye problem is provided that includes a holder for applying the apparatus to a person and a therapy unit that supplies a therapeutically effective dose of a magnetic field or electric current or both. In some embodiments, the therapy unit is operatively coupled to the holder so that the holder maintains the unit in a therapeutically effective position for treatment of the eye problem. In some embodiments, the therapy unit of the kit includes a magnet. In still further embodiments, the kit includes a holder with a bio-compatible releasable adhesive for holding at least a portion of the magnet against the skin of a lower eyelid. In some embodiments, a skin-contact surface of the magnet is coated with a hypoallergenic material to prevent migration of material from the magnet to the user's skin. In some embodiments, the magnet in the kit is made of a magnetized synthetic rubber. In some embodiments, the therapy unit of the kit includes a transcutaneous electrical stimulation unit. In some embodiments, the therapy unit of the kit includes a transcutaneous electrical nerve stimulation unit. Other embodiments of the kit include the therapy unit with a magnet. In some embodiments, the kit and the holder include eyeglasses.

In some embodiments, an apparatus for the treatment of an eye problem is disclosed that includes a holder for applying the apparatus to a person, a therapy unit that supplies a therapeutically effective dose of a magnetic field or electric current or both. This unit, in some embodiments, is operatively coupled to the holder so that the holder maintains the unit in a therapeutically effective position for treatment of the eye problem. In some embodiments, holder includes eyeglasses. In some embodiments, the holder includes a transcutaneous electrical stimulation unit that applies small electrical pulses to the user's skin just below the eye. In some embodiments, a magnet encased in a sterile bio-compatible plastic material is implanted just under the skin. In still other embodiments, a therapy unit includes a magnet, a bio-compatible releasable adhesive for holding at least a portion of the magnet against the skin of a lower eyelid, and a skin-contact surface of the magnet coated with a hypoallergenic material to prevent migration of material from the magnet to a user's skin. In some embodiments, the therapy unit including a thermal compress. In some embodiments, the magnet is made of a rare earth metal such as Neodymium.

In some embodiments, a therapy unit including a battery operatively coupled to an electromagnet is provided. In some embodiments, the therapy unit includes a heating element operatively coupled to the battery. In some embodiments, electrical current from the battery is controlled by a switch. In some embodiments, the therapy unit is operatively coupled to eyeglasses.

In some embodiments, a therapy unit including: a first layer of hypoallergenic material, a second layer attached to the first layer, where the second layer includes an electromagnet, a third layer attached to the second layer, the third layer having a battery operatively connected to the electromagnet in the second layer. In some embodiments, a fourth optional layer secured to the third layer, the fourth layer having a heating element operatively connected to the battery of the third layer, and a fifth optional layer secured to the fourth containing a tapping device operatively connected to the battery of the third layer is also included. In some embodiments of the therapy unit, the first layer includes a micropore-type tape. In some embodiments, the therapy unit is operative connected to a user's skin with an adhesive material. In some embodiments, the battery of the therapy unit is controlled by a switch. In some embodiments, the therapy unit is operatively coupled to eyeglasses.

In some embodiments, a method of treating an eye problem, is used that includes applying a field to an outer surface of an eyelid of a person with an eye problem, maintaining the field in position as the person uses an eye for seeing, and maintaining of the field in a position including adhering a lower edge and at least one side edge but not a top edge of a therapy unit to the lower eyelid of the person. In some embodiments, the therapy unit is operatively coupled to eyeglasses.

In some embodiments, an apparatus for treating an eye problem, the apparatus includes a means for generating a field; and an adhering means to maintain the field in a therapeutically effective position for treatment of the eye problem. In still other embodiments, a means for attaching the apparatus to a pair of eyeglasses.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus for the treatment of an eye problem of a user person, the apparatus comprising:

a therapy unit that supplies a floater-controlling therapeutically effective dose of a magnetic field, or both the magnetic field and an electric stimulation; and a holder operatively coupled to the therapy unit so that the holder maintains the therapy unit in a therapeutically effective position on the person near the person's eye, wherein the holder includes a bio-compatible adhesive material configured to hold the therapy unit to but readily release from the user's skin, and wherein the therapy unit and the holder are assembled into a single unit operatively configured to be used alone and held to the person's skin on only a lower eyelid of the person, wherein the holder includes a first surface facing away from the user's skin and a second surface facing toward the user's skin, the second surface having an area, wherein the therapy unit includes a permanent magnet and the adhesive material is affixed to a lower edge of the second surface, and at least one side edge but not a top edge of the second surface, and at least half the area of the second surface is free of adhesive when the adhesive material on the lower edge is adhered to the lower eyelid of the user.

2. The apparatus of claim 1, wherein the permanent magnet includes a magnetized synthetic rubber.

3. The apparatus of claim 1, wherein the permanent magnet includes a rare-earth metal.

4. The apparatus of claim 1, further comprising a battery and an electromagnet operatively coupled to the battery, wherein the magnetic field is produced, at least in part, by the electromagnet.

5. The apparatus of claim 4, further comprising a heating element operatively coupled to the battery.

6. The apparatus of claim 1, further comprising a transcutaneous electrical stimulation unit, wherein the electric stimulation is produced by the transcutaneous electrical stimulation unit.

7. The apparatus of claim 1, further comprising a transcutaneous electrical nerve stimulation unit, wherein the electric stimulation includes electric nerve stimulation produced by the transcutaneous electrical nerve stimulation unit.

8. The apparatus of claim 1, wherein the therapy unit includes a skin-contact surface and at least the skin-contact surface of the therapy unit is coated with a hypoallergenic material to prevent migration of material from the therapy unit to the user's skin.

9. The apparatus of claim 1, wherein the holder includes micropore-type tape.

10. An apparatus for the treatment of an eye problem of a person, the apparatus comprising:
a magnetic therapy unit consisting of a single magnet that supplies a floater-controlling therapeutically effective dose of a magnetic field; and
a holder operatively coupled to the therapy unit so that the holder is adapted to maintain the magnetic therapy unit in a therapeutically effective position against skin of a lower eyelid the person, wherein the holder includes eyeglasses, and wherein the magnet of the therapy unit is only near the lower rim of the eyeglasses and the holder is configured to hold the magnet of the magnetic therapy unit against the lower eyelid of the person.

11. The apparatus of claim 10, wherein the magnetic therapy unit is adapted to be held against the lower eyelid of the person by rim holders.

12. An apparatus for the treatment of an eye problem of a person, the apparatus comprising:
a therapy unit that supplies a floater-controlling therapeutically effective dose of a magnetic field, or both the magnetic field and an electric stimulation;
a holder operatively coupled to the therapy unit so that the holder maintains the therapy unit in a therapeutically effective position on the person near the person's eye, wherein the holder includes a bio-compatible adhesive material configured to hold the therapy unit to but readily release from the user's skin, and wherein the therapy unit and the holder are assembled into a single unit operatively configured to be used alone and held to the person's skin on only a lower eyelid of the person, wherein the holder includes a first surface facing away from the user's skin and a second surface facing toward the user's skin, the second surface having an area, wherein the therapy unit includes a permanent magnet and the adhesive material is affixed to a lower edge of the second surface, and at least one side edge but not a top edge of the second surface, and at least half the area of the second surface is free of adhesive when the adhesive material on the lower edge is adhered to the lower eyelid of the user; and
an electronically powered tapping unit configured to periodically apply a tapping force the area next to the user's eye.

13. A method of treating an eye problem that includes floaters, the method comprising:
applying a floater-controlling therapeutically effective dose of a field from a therapy unit to an outer surface of skin of a lower eyelid of an eye of a person; and
maintaining the field so that the field is applied from only below the eye in a therapeutically-effective position below the eye as the person uses the eye for seeing, wherein the field includes a magnetic component or both the magnetic component and an electric stimulation component, wherein the therapy unit includes a magnet, wherein the therapy unit has a first surface facing away from the user's skin and a second surface facing toward the user's skin, the second surface having an area, wherein the maintaining of the field in the therapeutically-effective position includes adhering a lower edge and at least one side edge but not a top edge of the second surface of the therapy unit to the lower eyelid of the person, and wherein at least half of the area of the second surface of the therapy unit is not adhered to the person.

14. A method of treating an eye problem that includes floaters, the method comprising:
applying a floater-controlling therapeutically effective dose of a field from a therapy unit to an outer surface of skin of a lower eyelid of an eye of a person;
maintaining the field so that the field is applied from only below the eye in a therapeutically-effective position below the eye as the person uses the eye for seeing, wherein the field includes a magnetic component, or both the magnetic component and an electric stimulation component, wherein the therapy unit includes a magnet, wherein the therapy unit has a first surface facing away from the user's skin and a second surface facing toward the user's skin, the second surface having an area, wherein the maintaining of the field in the therapeutically-effective position includes adhering a lower edge and at least one side edge but not a top edge of the second surface of the therapy unit to the lower eyelid of the person, and wherein at least half of the area of the second surface of the therapy unit is not adhered to the person;
applying a tapping force to the area next to the user's eye; and
electronically controlling the tapping force.

15. An apparatus for treating a problem of an eye of a person, the apparatus comprising:
means for generating a therapeutically effective floater-controlling magnetic field; and
means for maintaining the field in a therapeutically effective position against a lower eyelid of the person for treatment of the eye problem as the person uses the eye for seeing, wherein the means for generating the therapeutically effective floater-controlling magnetic field includes a magnet, wherein the means for maintaining the field in the therapeutically effective position has a first surface facing away from the user's skin and a second surface having an area facing toward the user's skin, wherein the means for maintaining the field includes adhesive on a lower edge and at least one side edge but not a top edge of the second surface of the means for maintaining the field, and wherein at least half of the area of the second surface of the means for maintaining the field is not adhered to the person.

16. The apparatus of claim 15 comprising means for applying a tapping force to an area next to the user's eye.

* * * * *